United States Patent [19]
Komiyama et al.

[11] Patent Number: 5,942,488
[45] Date of Patent: Aug. 24, 1999

[54] HAEMOGLOBIN

[75] Inventors: Noboru Komiyama; Kiyoshi Nagai, both of Cambridge, United Kingdom

[73] Assignee: Baxter Biotech Technology Sarl, Neuchatel, Switzerland

[21] Appl. No.: 08/619,708

[22] PCT Filed: Sep. 13, 1994

[86] PCT No.: PCT/GB94/01996

§ 371 Date: Jun. 17, 1996

§ 102(e) Date: Jun. 17, 1996

[87] PCT Pub. No.: WO95/07932

PCT Pub. Date: Mar. 23, 1995

[30] Foreign Application Priority Data

Sep. 14, 1993 [GB] United Kingdom ............ 9318974
Jul. 22, 1994 [GB] United Kingdom ............ 9414772

[51] Int. Cl.$^6$ .................... A61K 38/92; C07K 14/805
[52] U.S. Cl. .................... 514/6; 530/385; 435/172.3; 435/68.1
[58] Field of Search .............. 435/172.3; 530/385; 514/6

[56] References Cited

PUBLICATIONS

Bauer & Jelkmann/Carbon Dioxide Governs the Oxygen Affinity of Crocodile Blood/ Nature/1977/269: 828–827.

Leclercq et al/Direct Reciprocal Allosteric Interaction of Oxygen and Hydrogen Carbonate Sequence of Haemoglobins of the Caiman (Caiman Crodocylus), The Nile Crocodile (Crocodylus Niloticus) and the Mississippi Crocodile (Alligator Mississippiensis) Hoppe–Seyler's Z. Physiol. Chem./1981/Bd. 362,S: 1151–1158.

Kilmartin & Rossi–Bernardi/Inhibition of $CO_2$ Combination and Reduction of Bohr Effect in Haemoglobin Chemically Modified at its α–Amino Groups/Nature/1969/222: 1243–1246.

Perutz Et Al/Allosteric Regulation of Crocodilian Haemoglobin/Nature/1981/291: 682–684.

Looker et al/A Human Recombinant Haemoglobin Designed for use as a Blood Substitute/Nature/1992/356: 258–260.

Bauer et al/Analysis of Bicarbonate Binding to Crocodilian Hemoglobin/J. of Biological Chemistry/1981/256(16) 8429–8435.

*Primary Examiner*—Cecilia J. Tsang
*Assistant Examiner*—Michael Borin
*Attorney, Agent, or Firm*—Senniger, Powers, Leavitt & Roedel

[57] ABSTRACT

Disclosed is a mutant human β globin modified so as to exhibit, when present as part of a hemoglobin molecule, an altered bicarbonate effect compared to the unmodified β globin. The β globin is modified to contain at positions 29–41 at least two non-wild type amino acid residues selected from the group consisting of amino acid residues 29–41 of crocodile β-globin SEQ ID NO:2 to produce an enhanced bicarbonate effect.

6 Claims, 7 Drawing Sheets

FIG. 1

```
* Alpha-globin
   M   L   S   S   D   D   K   C   N   V   K   A   V   W   S   K   V   A   G   H
ATGCTGTCTTCTGACGACAAATGCAACGTTAAAGCTGTTTGGTCTAAAGTTGCTGGTCAC
       10          20          30          40          50          60

L   E   E   Y   G   A   E   A   L   E   R   M   F   C   A   Y   P   Q   T   K
CTGGAAGAATACGGTGCTGAAGCTCTCGAGCGTATGTTCTGCGCTTACCCGCAGACTAAA
       70          80          90         100         110         120

I   Y   F   P   H   F   D   L   S   H   G   S   A   Q   I   R   A   H   G   K
ATCTACTTCCCGCACTTCGACCTGTCTCACGGTTCTGCGCAGATCCGTGCTCACGGTAAA
      130         140         150         160         170         180

K   V   F   A   A   L   H   E   A   V   N   H   I   D   D   L   P   G   A   L
AAAGTTTTCGCTGCTCTGCACGAAGCTGTAAACCACATCGACGACCTGCCGGGTGCTCTG
      190         200         210         220         230         240

C   R   L   S   E   L   H   A   H   S   L   R   V   D   P   V   N   F   K   F
TGCCGTCTGTCTGAACTGCACGCTCACTCTCTGCGTGTGGATCCGGTTAACTTCAAATTC
      250         260         270         280         290         300

L   A   Q   C   V   L   V   V   V   A   I   H   H   P   G   S   L   T   P   E
CTGGCTCAGTGCGTTCTGGTTGTTGTTGCTATCCACCATCCGGGTTCTCTGACTCCGGAA
      310         320         330         340         350         360

V   H   A   S   L   D   K   F   L   C   A   V   S   S   V   L   T   S   K   Y
GTTCACGCGTCTCTGGACAAATTCCTGTGCGCTGTTTCTTCTGTTCTGACTTCTAAATAC
      370         380         390         400         410         420

R
CGT
```

FIG. 1A

```
* Beta-globin
  M   S   F   D   P   H   E   K   Q   L   I   G   D   L   W   H   K   V   D   V
ATGTCTTTCGACCCGCACGAAAAACAGCTGATCGGTGACCTGTGGCACAAAGTTGACGTT
        10        20        30        40        50        60

A   H   C   G   G   E   A   L   S   R   M   L   I   V   Y   P   W   K   R   R
GCTCACTGCGGTGGTGAGGCCTTGTCTCGTATGCTGATCGTTTACCCGTGGAAACGTCGT
        70        80        90       100       110       120

Y   F   E   N   F   G   D   I   S   N   A   Q   A   I   M   H   N   E   K   V
TACTTCGAAAACTTCGGTGATATCTCTAACGCTCAGGCTATCATGCACAACGAAAAAGTT
       130       140       150       160       170       180

Q   A   H   G   K   K   V   L   A   S   F   G   E   A   V   C   H   L   D   G
CAGGCCCAATGGTAAAAAAGTTCTGGCTTCTTTCGGTGAAGCTGTTTGCCACCTGGACGGT
       190       200       210       220       230       240

I   R   A   H   F   A   N   L   S   K   L   H   C   E   K   L   H   V   D   P
ATCCGTGCTCACTTCGCTAACCTGTCTAAACTGCACTGCGAAAAACTGCACGTGGATCCG
       250       260       270       280       290       300

E   N   F   K   L   L   G   D   I   I   I   I   V   L   A   A   H   Y   P   K
GAAAACTTCAAACTGCTGGGTGACATCATCATCATCGTGCTAGCTGCTCACTACCCGAAA
       310       320       330       340       350       360

D   F   G   L   E   C   H   A   A   Y   Q   K   L   V   R   Q   V   A   A   A
GACTTCGGTCTGGAATGCCACGCTGCTTACCAGAAACTGGTTCGTCAGGTTGCTGCTGCT
       370       380       390       400       410       420

L   A   A   E   Y   H
CTGGCTGCTGAATACCAC
       430
```

FIG. 2
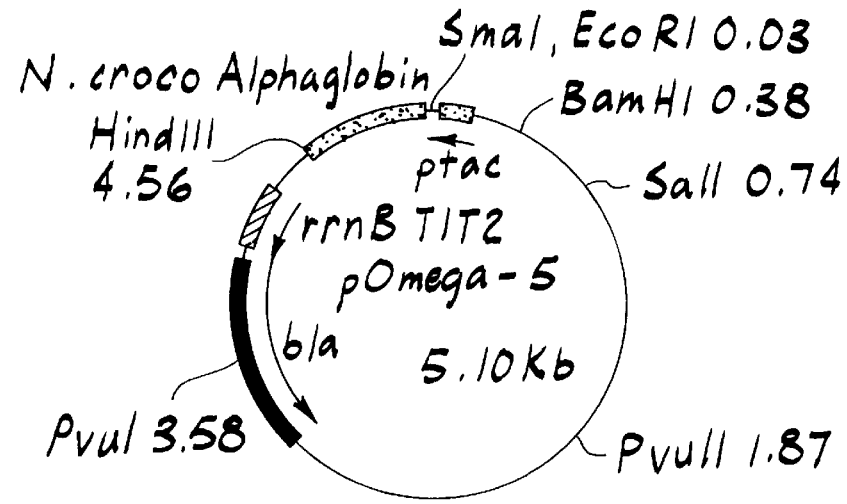
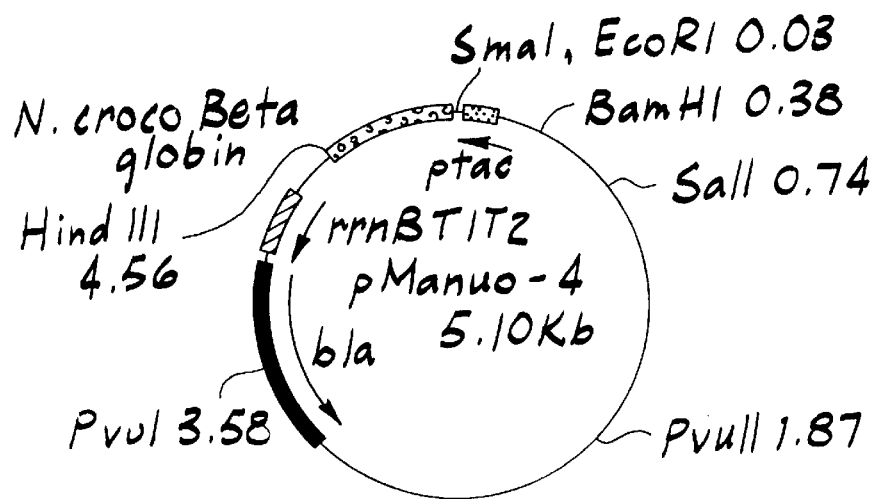
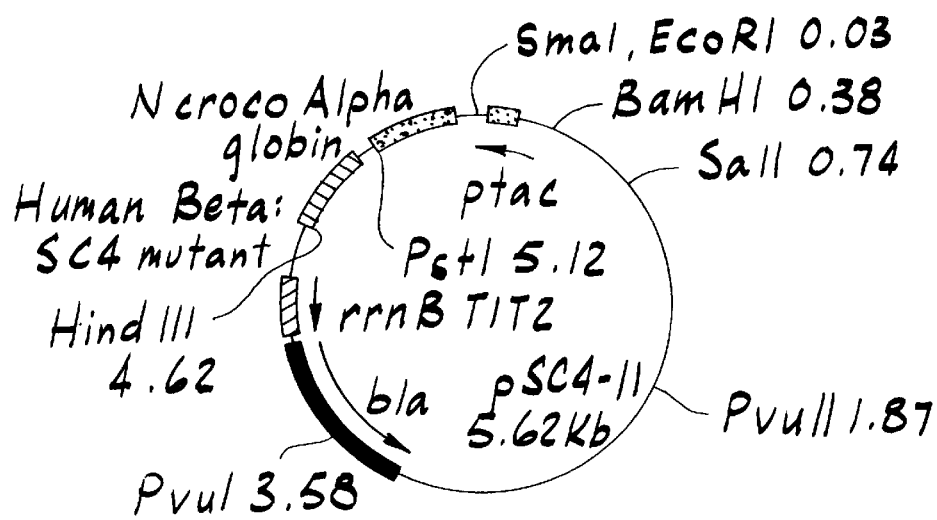

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 423bp
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:1:

```
ATG CTG TCT TCT GAC GAC AAA TGC AAC GTT AAA GCT GTT TGG TCT AAA          48
Met Leu Ser Ser Asp Asp Lys Cys Asn Val Lys Ala Val Trp Ser Lys
 1               5                  10                  15

GTT GCT GGT CAC CTG GAA GAA TAC GGT GCT GAA GCT CTC GAG CGT ATG          96
Val Ala Gly His Leu Glu Glu Tyr Gly Ala Glu Ala Leu Glu Arg Met
                20                  25                  30

TTC TGC GCT TAC CCG CAG ACT AAA ATC TAC TTC CCG CAC TTC GAC CTG         144
Phe Cys Ala Tyr Pro Gln Thr Lys Ile Tyr Phe Pro His Phe Asp Leu
            35                  40                  45

TCT CAC GGT TCT GCG CAG ATC CGT GCT CAC GGT AAA AAA GTT TTC GCT         192
Ser His Gly Ser Ala Gln Ile Arg Ala His Gly Lys Lys Val Phe Ala
        50                  55                  60

GCT CTG CAC GAA GCT GTA AAC CAC ATC GAC GAC CTG CCG GGT GCT CTG         240
Ala Leu His Glu Ala Val Asn His Ile Asp Asp Leu Pro Gly Ala Leu
65                  70                  75                  80

TGC CGT CTG TCT GAA CTG CAC GCT CAC TCT CTG CGT GTG GAT CCG GTT         288
Cys Arg Leu Ser Glu Leu His Ala His Ser Leu Arg Val Asp Pro Val
                85                  90                  95

AAC TTC AAA TTC CTG GCT CAG TGC GTT CTG GTT GTT GTT GCT ATC CAC         336
Asn Phe Lys Phe Leu Ala Gln Cys Val Leu Val Val Val Ala Ile His
            100                 105                 110

CAT CCG GGT TCT CTG ACT CCG GAA GTT CAC GCG TCT CTG GAC AAA TTC         384
His Pro Gly Ser Leu Thr Pro Glu Val His Ala Ser Leu Asp Lys Phe
        115                 120                 125

CTG TGC GCT GTT TCT TCT GTT CTG ACT TCT AAA TAC CGT                     423
Leu Cys Ala Val Ser Ser Val Leu Thr Ser Lys Tyr Arg
    130                 135                 140
```

(2) INFORMATION FOR SEQ ID NO:2:

(i) SEQUENCE CHARACTERISTICS:
      (A) LENGTH: 141
      (B) TYPE: amino acid
      (D) TOPOLOGY: linear (ii) MOLECULE TYPE: peptide (xi) SEQUENCE DESCRIPTION: SEQ ID NO:2:

```
Met Leu Ser Ser Asp Asp Lys Cys Asn Val Lys Ala Val Trp Ser Lys
 1               5                  10                  15

Val Ala Gly His Leu Glu Glu Tyr Gly Ala Glu Ala Leu Glu Arg Met
                 20                  25                  30

Phe Cys Ala Tyr Pro Gln Thr Lys Ile Tyr Phe Pro His Phe Asp Leu
             35                  40                  45

Ser His Gly Ser Ala Gln Ile Arg Ala His Gly Lys Lys Val Phe Ala
         50                  55                  60

Ala Leu His Glu Ala Val Asn His Ile Asp Asp Leu Pro Gly Ala Leu
 65                  70                  75                  80

Cys Arg Leu Ser Glu Leu His Ala His Ser Leu Arg Val Asp Pro Val
                 85                  90                  95

Asn Phe Lys Phe Leu Ala Gln Cys Val Leu Val Val Ala Ile His
             100                 105                 110

His Pro Gly Ser Leu Thr Pro Glu Val His Ala Ser Leu Asp Lys Phe
         115                 120                 125

Leu Cys Ala Val Ser Ser Val Leu Thr Ser Lys Tyr Arg
130                 135                 140
```

(2) INFORMATION FOR SEQ ID NO:3:

(i) SEQUENCE CHARACTERISTICS:
        (A) LENGTH: 438bp
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:3:

```
ATG TCT TTC GAC CCG CAC GAA AAA CAG CTG ATC GGT GAC CTG TGG CAC     48
Met Ser Phe Asp Pro His Glu Lys Gln Leu Ile Gly Asp Leu Trp His
 1               5                  10                  15

AAA GTT GAC GTT GCT CAC TGC GGT GGT GAG GCC TTG TCT CGT ATG CTG     96
Lys Val Asp Val Ala His Cys Gly Gly Glu Ala Leu Ser Arg Met Leu
                 20                  25                  30

ATC GTT TAC CCG TGG AAA CGT CGT TAC TTC GAA AAC TTC GGT GAT ATC    144
Ile Val Tyr Pro Trp Lys Arg Arg Tyr Phe Glu Asn Phe Gly Asp Ile
             35                  40                  45

TCT AAC GCT CAG GCT ATC ATG CAC AAC GAA AAA GTT CAG GCC CAT GGT    192
Ser Asn Ala Gln Ala Ile Met His Asn Glu Lys Val Gln Ala His Gly
         50                  55                  60

AAA AAA GTT CTG GCT TCT TTC GGT GAA GCT GTT TGC CAC CTG GAC GGT    240
Lys Lys Val Leu Ala Ser Phe Gly Glu Ala Val Cys His Leu Asp Gly
 65                  70                  75                  80

ATC CGT GCT CAC TTC GCT AAC CTG TCT AAA CTG CAC TGC GAA AAA CTG    288
Ile Arg Ala His Phe Ala Asn Leu Ser Lys Leu His Cys Glu Lys Leu
                 85                  90                  95

CAC GTG GAT CCG GAA AAC TTC AAA CTG CTG GGT GAC ATC ATC ATC ATC    336
His Val Asp Pro Glu Asn Phe Lys Leu Leu Gly Asp Ile Ile Ile Ile
             100                 105                 110

GTG CTA GCT GCT CAC TAC CCG AAA GAC TTC GGT CTG GAA TGC CAC GCT    384
Val Leu Ala Ala His Tyr Pro Lys Asp Phe Gly Leu Glu Cys His Ala
         115                 120                 125

GCT TAC CAG AAA CTG GTT CGT CAG GTT GCT GCT GCT CTG GCT GCT GAA    432
Ala Tyr Gln Lys Leu Val Arg Gln Val Ala Ala Ala Leu Ala Ala Glu
130                 135                 140

TAC CAC                                                            438
Tyr His
145
```

(2) INFORMATION FOR SEQ ID NO:4:

(i) SEQUENCE CHARACTERISTICS:
        (A) LENGTH: 146aa
        (B) TYPE: amino acid
        (D) TOPOLOGY: linear (ii) MOLECULE TYPE: peptide (xi) SEQUENCE DESCRIPTION: SEQ ID NO:4:

```
Met Ser Phe Asp Pro His Glu Lys Gln Leu Ile Gly Asp Leu Trp His
 1               5                  10                  15

Lys Val Asp Val Ala His Cys Gly Gly Glu Ala Leu Ser Arg Met Leu
                20                  25                  30

Ile Val Tyr Pro Trp Lys Arg Arg Tyr Phe Glu Asn Phe Gly Asp Ile
            35                  40                  45

Ser Asn Ala Gln Ala Ile Met His Asn Glu Lys Val Gln Ala His Gly
59                      55                      60

Lys Lys Val Leu Ala Ser Phe Gly Glu Ala Val Cys His Leu Asp Gly
65                      70                      75              80

Ile Arg Ala His Phe Ala Asn Leu Ser Lys Leu His Cys Glu Lys Leu
                85                  90                  95

His Val Asp Pro Glu Asn Phe Lys Leu Leu Gly Asp Ile Ile Ile Ile
            100                 105                 110

Val Leu Ala Ala His Tyr Pro Lys Asp Phe Gly Leu Glu Cys His Ala
            115                 120                 125

Ala Tyr Gln Lys Leu Val Arg Gln Val Ala Ala Leu Ala Ala Glu
    130                 135                 140

Tyr His
145
```

(2) INFORMATION FOR SEQ ID NO:5:

(i) SEQUENCE CHARACTERISTICS:
        (A) LENGTH: 141
        (B) TYPE: amino acid
        (D) TOPOLOGY: linear (ii) MOLECULE TYPE: protein (xi) SEQUENCE DESCRIPTION: SEQ ID NO:5:

```
Val Leu Ser Pro Ala Asp Lys Thr Asn Val Lys Ala Ala Trp Gly
5                   10                  15

Lys Val Gly Ala His Ala Gly Glu Tyr Gly Ala Glu Ala Leu Glu
                20                  25                  30

Arg Met Phe Leu Ser Phe Pro Thr Thr Lys Thr Tyr Phe Pro His
            35                  40                  45

Phe Asp Leu Ser His Gly Ser Ala Gln Val Lys Gly His Gly Lys
50                      55                      60

Lys Val Ala Asp Ala Leu Thr Asn Ala Val Ala His Val Asp Asp
65                      70                      75

Met Pro Asn Ala Leu Ser Ala Leu Ser Asp Leu His Ala His Lys
                80                  85                  90

Leu Arg Val Asp Pro Val Asn Phe Lys Leu Leu Ser His Cys Leu
            95                  100                 105

Leu Val Thr Leu Ala Ala His Leu Pro Ala Glu Phe Thr Pro Ala
            110                 115                 120

Val His Ala Ser Leu Asp Lys Phe Leu Ala Ser Val Ser Thr Val
            125                 130                 135
```

```
Leu Thr Ser Lys Tyr Arg
140

(2) INFORMATION FOR SEQ ID NO:6:

(i) SEQUENCE CHARACTERISTICS:
        (A) LENGTH:  146
        (B) TYPE:  amino acid
        (D) TOPOLOGY:  unknown to applicant (ii) MOLECULE TYPE:  protein (iii) HYPOTHETICAL:  no (xi) SEQUENCE DESCRIPTION:  SEQ ID NO:6:

Val His Leu Thr Pro Glu Glu Lys Ser Ala Val Thr Ala Leu Trp
 5              10                  15

Gly Lys Val Asn Val Asp Glu Val Gly Gly Glu Ala Leu Gly Arg
            20                  25                  30

Leu Leu Val Val Tyr Pro Trp Thr Gln Arg Phe Phe Glu Ser Phe
            35                  40                  45

Gly Asp Leu Ser Thr Pro Asp Ala Val Met Gly Asn Pro Lys Val
50                  55                  60

Lys Ala His Gly Lys Lys Val Leu Gly Ala Phe Ser Asp Gly Leu
65                  70                  75

Ala His Leu Asp Asn Leu Lys Gly Thr Phe Ala Thr Leu Ser Glu
            80                  85                  90

Leu His Cys Asp Lys Leu His Val Asp Pro Glu Asn Phe Arg Leu
            95                  100                 105

Leu Gly Asn Val Leu Val Cys Val Leu Ala His Phe Gly Lys
            110                 115                 120

Glu Phe Thr Pro Pro Val Gln Ala Ala Tyr Gln Lys Val Val Ala
            125                 130                 135

Gly Val Ala Asn Ala Leu Ala His Lys Tyr His
140                 145

(2) INFORMATION FOR SEQ ID NO:7:

(i) SEQUENCE CHARACTERISTICS:
        (A) LENGTH:  146
        (B) TYPE:  amino acid
        (D) TOPOLOGY:  unknown to applicant (ii) MOLECULE TYPE:  protein (iii) HYPOTHETICAL:  no (xi) SEQUENCE DESCRIPTION:  SEQ ID NO:7:

Val His Leu Thr Pro Glu Glu Lys Ser Ala Val Thr Ala Leu Trp
 5              10                  15

Gly Lys Val Asn Val Asp Glu Val Gly Gly Glu Ala Leu Ser Arg
            20                  25                  30

Met Leu Ile Val Tyr Pro Trp Lys Arg Arg Tyr Phe Glu Ser Phe
            35                  40                  45

Gly Asp Leu Ser Thr Pro Asp Ala Val Met Gly Asn Pro Lys Val
50                  55                  60

Lys Ala His Gly Lys Lys Val Leu Gly Ala Phe Ser Asp Gly Leu
65                  70                  75

Ala His Leu Asp Asn Leu Lys Gly Thr Phe Ala Thr Leu Ser Glu
            80                  85                  90
```

```
Leu His Cys Asp Lys Leu His Val Asp Pro Glu Asn Phe Arg Leu
            95              100                 105

Leu Gly Asn Val Leu Val Cys Val Leu Ala His His Phe Gly Lys
        110             115             120

Glu Phe Thr Pro Pro Val Gln Ala Ala Tyr Gln Lys Val Val Ala
    125             130             135

Gly Val Ala Asn Ala Leu Ala His Lys Tyr His
140             145
```

HAEMOGLOBIN

FIELD OF THE INVENTION

This invention relates to improved forms of haemoglobin and to improved blood substitutes comprising haemoglobin.

BACKGROUND TO THE INVENTION

All vertebrate haemoglobins (Hb) are tetramers consisting of two alpha (α) globin chains and two beta (β) globin sub-units each carrying an iron-containing prosthetic group, haem. The oxygen binding to the four sub-units within the tetramer is co-operative (ie binding of oxygen at one haem group facilitates the binding of oxygen at the other haem groups on the same globin tetramer and conversely, the unloading of oxygen at one haem unit facilitates the unloading of oxygen at the others).

During vertebrate evolution the amino acid sequence of globins has diverged considerably, and the sequence identity between Hbs from the most distantly-related vertebrate species, (eg human and fish), is only about 50%. That between human and crocodile haemaglobins, for example, is about 60%. Despite this sequence variation, vertebrate Hbs have generally retained their tertiary and quaternary structures (Camardella et al., 1992 J. Mol. Biol. 224, 449–460) and the key residues necessary for haem-haem interaction.

The oxygen affinity of human Hb is modulated by various metabolites, such as 2,3-diphosphoglycerate (DPG) and $H^+$. They facilitate unloading of oxygen to actively respiring tissues. This general phenomenon is called the heterotropic allosteric effect.

In particular, the oxygen affinity of Hb is affected by the concentration of $CO_2$, such that high concentrations of $CO_2$, (with a partial pressure, "$PCO_2$" of about 40 mm Hg, as will be found in actively respiring tissues) cause a reduction in the oxygen affinity, thereby facilitating the unloading of oxygen to the tissues. This phenomenon is known as the $CO_2$ effect. In human Hb, $CO_2$ binds directly to the α-amino groups of the α and β globin submits to form carbamino groups and reduces the oxygen affinity by stabilising the low affinity (T) quaternary structure (Kilmartin & Rossi-Bernardi, 1969 Nature 222, 1243–1246). The $CO_2$ effect is one of the principal heterotropic allosteric effects.

Vertebrate species have adapted to strikingly diverse environmental conditions, and the haemoglobin molecule has evolved to meet a wide range of respiratory needs in such environments. For example, the oxygen affinity of crocodile Hb is marketly reduced by physiological concentrations of $CO_2$ (40 torr). Bauer et al. (1981, J. Biol. Chem. 256, 8429–8435) showed that the large reduction in the oxygen affinity of crocodile Hb is not caused by the binding of $CO_2$ to the α amino groups as in human Hb. Carbon dioxide ($CO_2$) dissolves in aqueous solutions (such as blood) to give $HCO_3^-$. The marked reduction in the oxygen affinity in crocodile Hb is caused by the binding of bicarbonate ions and this phenomenon is called the "bicarbonate effect". A much larger proportion of Hb-bound oxygen can be released and utilised in the tissues and this enables crocodiles to stay under water for a long time. It has been postulated (Perutz et al., 1981 Natue 291, 682–684) that this effect is due to bicarbonate ions binding to residues Lys 82 and Glu 144 of the β globin molecule.

There is interest in developing "artificial blood" products. Such products would eliminate the chance of infection due to a patient receiving infected blood from a donor, and generally simplify the blood transfusion process. Clearly, in order to perform all the functions of natural blood, the artificial product must be capable of transporting oxygen.

Unfortunately, haemoglobin outside the environment of a red blood cell (RBC) has too high an affinity to release much oxygen to the tissues. This is because RBCs contain large amounts of DPG which, as mentioned above, is one of the metabolites which lowers the oxygen affinity of Hb.

Consequently, there is a need for a stable, artificial blood product with improved oxygen affinity characteristics which will deliver oxygen more effectively to respiring tissues.

SUMMARY OF THE INVENTION

In a first aspect the invention provides a β globin modified so as to exhibit, when present as part of a haemoglobin molecule, an altered bicarbonate effect compared to the unmodified β globin, the modification comprising alteration of at least two of the amino acid residues in the group consisting of residues 29–41.

It was found by the present inventors that human haemoglobin comprising β globin subunits altered in accordance with the invention, by substitution with equivalent crocodile β globin residues, exhibited a greatly enhanced bicarbonate effect analogous to that displayed by native crocodile haemoglobin. This is surprising because haemoglobin is a complex tetrameric molecule with prosthetic groups, yet very small changes in just the β globin primary structure in α (crocodile) β (human) haemoglobin can cause large changes in the bicarbonate effect, whilst the α globin and prosthetic groups are unaltered.

Further, most of residues 29–41 of β globin are located at the interface of the $α_1/β_2$ globin subunits and changes therein might thus be expected to cause the molecule to lose stability or permanently reduce its oxygen affinity. It was surprisingly found, however, that an alteration in accordance with the invention did not cause such deleterious effects.

In a second aspect the invention provides a method of modifying a β globin so as to exhibit, when present as part of an haemoglobin molecule, an altered bicarbonate effect compared to the unmodified β globin, the modification comprising substitution of at least two of the amino acid residues in the group consisting of residues 29–41.

Preferably the β globin is human β globin. Preferably the β globin is modified so as to exhibit an enhanced bicarbonate efect (ie a greater decrease in oxygen affinity in the presence of aqueous carbon dioxide) compared to the unmodified β globin.

It is preferred that the at least two altered amino acid residues comprise at least two residues from the group consisting of residues 29, 31, 33, 38, 39 and 41. Most preferably the modification comprises substitution of residues 38 and 41.

In a preferred embodiment, residues 29–41 of human β globin are replaced with the equivalent residues from crocodile β globin. It will be apparent to those skilled in the art that some of the amino acid residues are common to the Hb of both species. Accordingly, it is not necessary to alter all the residues 29–41 but simply those residues which are not common to both (ie residues 29, 31, 33, 38, 39 and 41). Moreover residues Ser 29 β and Met 31 β are not in the α1 β2 contact and substitutions of these residues not be required in order to introduce the full bicarbonate effect.

In another aspect the invention provides a haemoglobin molecule for use as an artificial blood substitute, comprising a β globin modified so as to exhibit an altered bicarbonate effect compared to a haemoglobin molecule comprising an unmodified β globin, the modification comprising substitution of at least two of the amino acid residues in the group consisting of residues 29–41.

Conveniently the haemoglobin molecule also comprises a modified α globin chain.

Typically the α globin chain will comprise a substantially human α globin sequence modified at one or more residues so as to optimise the oxygen-transport characteristics of the haemoglobin molecule for use as an artifical blood substitute. Conveniently the α globin chain will be modified in a manner as disclosed in UK Patent Application No 9414772.5. or similar. so as to exhibit an altered bicarbonate effect compared to the unmodified α globin.

Conveniently the modified α globin will comprise an alteration at one or more of the following residues: 34, 35, 36, 37, 41, 100 and 103.

Desirably the modified α globin will comprise one or more (preferably all) of the following substitutions: Leu 34→Cys, Ser 35→Ala, Phe 36→Tyr, Thr 37→Gln, Thr 41→Ile. Leu 100→Phe and His 103→Gln.

In a further aspect. the invention provides an artificial blood substitute comprising the haemoglobin molecule defined above.

The invention will now be further described by way of illustrative example and by reference to the drawings.

BRIEF DESCRIPTION OF DRAWINGS

FIG. 1 shows the nucleotide sequences encoding the α and β globins of the Nile crocodile (as optimised for expression in $E.\ coli$) and the amino acid sequences of the encoded polypeptides;

FIG. 2 is a schematic representation of the crocodile α and β globin expression constructs pOmega-5 and pManuo-4, and of the hybrid expression construct pSC4-11;

EXAMPLE 1

Figure 3A:
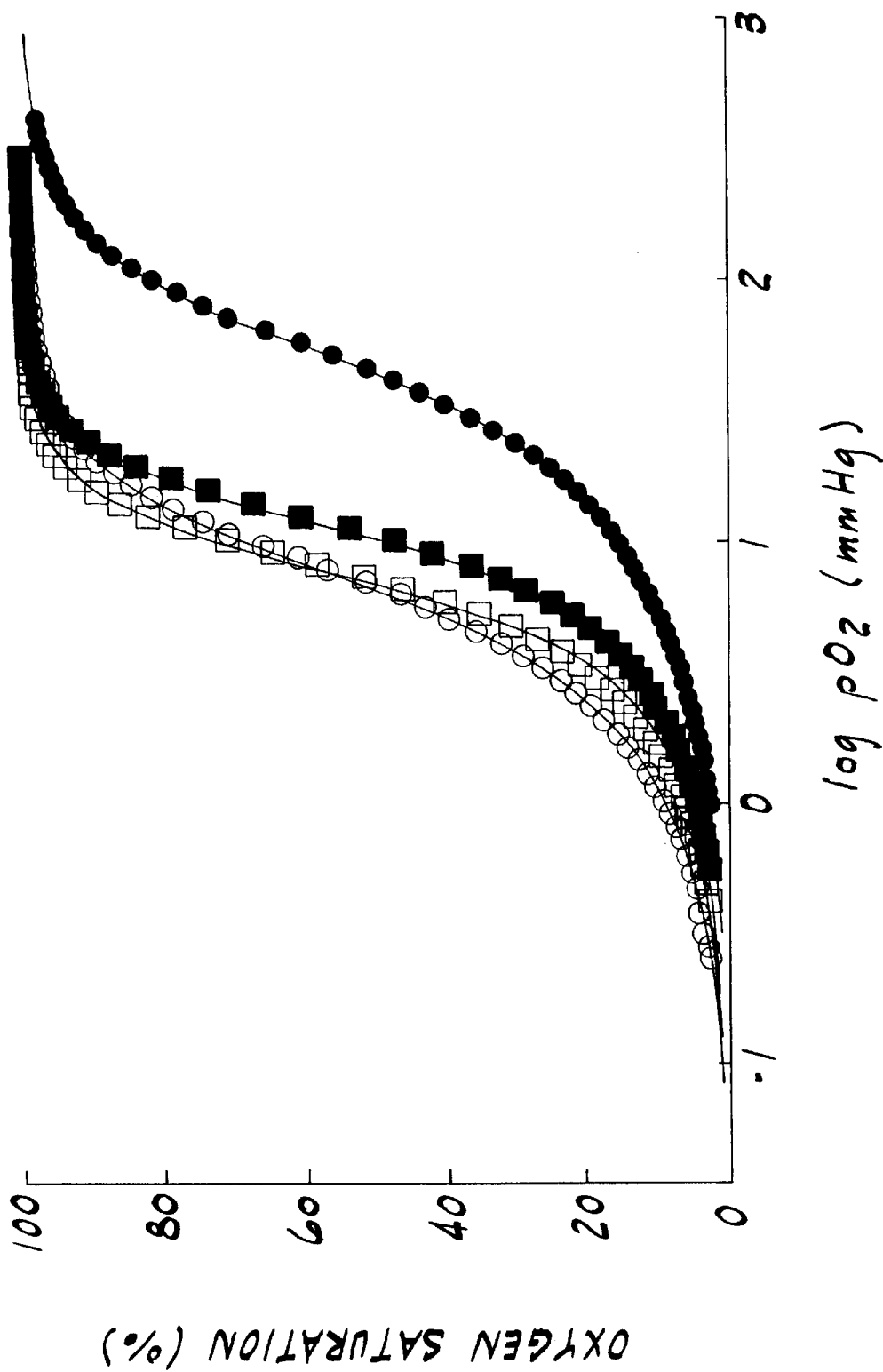
FIG. 3a is a graph of the oxygen binding curve (% $O_2$ saturation against log $_pO_2$ in mm Hg) for recombinant crocodile (circles) and human (squares) haemoglobins in the absence (open symbols) or presence (filled-in symbols) of 5% $CO_2$.

As described previously. Perutz et al. (1981, cited above) proposed bicarbonate ion binding sites to be located in the central cavity between two β subunits and to involve hydrogen bonds to Lys (82 β) and Glu (14 β) of one β subunit and the N-terminal residues of its partner. Four differences (relative to human haemoglobin) in crocodile Hb, His-143 β→Ala, Lys-144 β→Gly, Val-1 β→Ser and His-9 β→Pro, are thought to be important to promote formation of these hydrogen bonds. The present inventors first introduced these mutations into human β globin but the $CO_2$ effect was the same as in native human Hb. It was considered that some additional mutations may be needed to create the appropriate electrostatic environment for the interaction of these residues with bicarbonate ions. Accordingly, three additional mutations. Asp-94 β→to Glu, Glu-90 β→Lys and His-135 β→-Arg, were introduced into this mutant but they still failed to show a large bicarbonate effect in human Hb. At this stage this strategy was abandoned and it was decided to first make crocodile Hb in $E.\ coli$ and to find mutations which abolish the bicarbonate effect.

As a first step, protein coding sequences of Nile crocodile α and β globins were chemically synthesised by assembly of 14 oligonucleotides with codons optimal for expression in $E.\ coli$ (Ikemura et al., 1982 J. Mol. Biol. 158, 573–597). All mutations were introduced by cassette mutagenesis (Wells et al., 1985 Gene 34, 315). The synthetic α and β globin coding sequences, and the polypeptides encoded thereby, are shown in FIG. 1 and as Seq. ID Nos. 1–4 in the attached sequence listing. These genes were cloned separately into the Hb expression vector developed by Somatogen, (Hoffman et al., 1990 Proc Nat. Acad. Sci. USA 87 8521–8525). This vector was derived from pKK223-3 (available from Pharmacia). The expression constructs pOmega-5 and pManuo-4 (expressing the Nile crocodile α and β globin genes respectively, under the control of the tac promoter) are illustrated schematically in FIG. 2, together with the co-expression construct pSC4-11, described below. These expression vectors were also derived from pKK223-3. The method of their preparation will be apparent to those skilled in the art from the teaching disclosed herein in combination with the disclosures of Hoffman et al., (cited previously).

When α (crocodile) and β (crocodile) chains were co-expressed. the resulting $E.\ coli$ product was soluble, but brown. The haem group was either oxidised in vivo or an unnatural haem was incorporated into Hb. It has not been posible to produce either the α or β chain or human Hb in $E.\ coli$ unless they are co-expressed (Hoffman et al., 1990 cited above). However, when the crocodile α or β genes were expressed on their own in $E.\ coli$, soluble single chain Hbs were produced. Purification of recombinant haemoglobins was performed according, to the method of Komiyama et al., (1991 Nature 352, 49–351).

By co-expressing mixtures of human and crocodile α and β globins in $E.\ coli$, it was possible to obtain hybrid haemoglobin molecules: α (crocodile)$_2$/β (human)$_2$ and α (human)$_2$/β (crocodile)$_2$. These hybrids were compared with the "single species" molecules, α (human)$_2$/β (human)$_2$ and α (crocodile)$_2$/β (crocodile), which were made by mixing the respective chains.

Oxygen equilibrium curves were obtained using the automatic recording apparatus described by Imai (1981 Meth. Enzymol. 76, 438–449). All measurements were performed at pH7.4 in 50 mM bis-Tris with 0.1M Cl at 25° C., either in the presence or absence of 5% $CO_2$, which was in equilibrium with 21 mM bicarbonate ion in the buffer. The results are shown in Table I, which illustrates the oxygen affinity (as measured by P50 mmHg, i.e. the partial pressure of oxygen, in millimetres of mercury, at which the haemoglobin became 50% saturated with oxygen) for these molecules either in the absence of added $CO_2$ or in the presence of 5% added $CO_2$. The table also shows these values for two other haemoglobin molecules, α (crocodile)$_2$/β (SC4)$_2$ and α (crocodile)$_2$/β (crocodile: 82K-Q)$_2$, the significance of which is discussed below. The table also shows the value of Hill's coefficient (n) for each hybrid, which is a measure of the co-operativity of oxygen binding.

Table 1 shows that wild type human Hb shows only a small effect of $CO_2$. Kilmartin & Rossi-Bernardi (1969, cited previously) showed that this is due to carbamylation of α amino groups. As reported by Bauer & Jelkinan (1977 Nature 269, 825–827), the oxygen affinity of α (crocodile)

$_2/\beta$ (crocodile)$_2$ is reduced ten-fold by 5% $CO_2$. Bauer et al. (1981, cited previously) have shown that this large reduction in oxygen affinity is caused by binding two bicarbonate ions per molecule of crocodile Hb. In Perutz's model, residue Lys-82 β forms a salt bridge with a bicarbonate ion. The present inventors introduced the Lys-82 β to Gln mutation into Nile crocodile Hb [α (crocodile)$_2$/β (crocodile:82k-Q)$_2$] but the magnitude of the bicarbonate effect was only slightly reduced as shown by Table I.

This shows the bicarbonate ions do not bind to the site proposed by Perutz et al.

Table I shows that neither the α (crocodiile)$_2$/β (human)$_2$ nor the α (human)$_2$/β (crocodile)$_2$ hybrid molecule exhibited a large $CO_2$ effect. It therefore seemed that neither the α subunit nor the β subunit were largely responsible but that the bicarbonate ion binding site may be located at the subunit interface between the α and β subunits.

TABLE I

Oxygen binding parameters of engineered Hbs

| | with no $CO_2$ | | with 5% $CO_2$ | |
|---|---|---|---|---|
| | $P_{50}$ (mmHg) | n | $P_{50}$ 50 (mmHg) | n |
| α (human)$_2$ β (human)$_2$ | 6.7 | 2.6 | 10.0 | 2.6 |
| α (croco)$_2$ β (human)$_2$ | 1.4 | 1.8 | 1.4 | 1.7 |
| α (human)$_2$ β (croco)$_2$ | 8.6 | 1.6 | 16.6 | 2.0 |
| α (croco)$_2$ β (croco)$_2$ | 6.3 | 1.9 | 42.2 | 1.9 |
| α (croco)$_2$ β (SC4)$_2$ | 1.1 | 1.4 | 11.0 | 1.7 |
| α (croco)$_2$ β (croco:82K-Q)$_2$ | 12.0 | 1.9 | 43.0 | 1.9 |

TABLE II

Comparison of amino acid sequences of β subunits of human and crocodile Hb in the region between residues 29 and 41.

| crocodile | S | R | M | L | I | V | Y | P | W | K | R | R | Y |
|---|---|---|---|---|---|---|---|---|---|---|---|---|---|
| | | | * | | * | | * | | | * | * | | * |
| human β | G | R | L | L | V | V | Y | P | W | T | Q | R | F |
| Amino acid residue No | | 30 | | | | | | | | | | 40 | |

The globin sequences of crocodilian haemoglobins (caiman, Nile crocodile and Mississippi alligator) were compared with those of other vertebrate Hbs. Residues between 29 and 41 of β subunits (located at the $\alpha_1, \beta_2$ contacts), are all conserved in these three species and in particular, Arg-39 β and Tyr-41 β are found only in crocodilian Hbs. This region (29–41) of the human sequence was replaced with that of the crocodile sequence (Table II) in α (crocodile)$_2$ β (human)$_2$, and the resulting hybrid Hb, named α (croco)$_2$ β (SC4)$_2$, exhibited a large $CO_2$ effect, as shown in Table I. This hybrid haemoglobin was expressed by the construct pSC4-11 as shown in FIG. 2.

To further investigate these findings the inventors also introduced the Lys-38 β→Thr, Arg-39 β→Gln and Tyr-41β→Phe mutations into β(crocodile)$_2$ and these three mutations completely abolished the bicarbonate ion effect but the Arg-39 β→Gln mutation alone did not effect the bicarbonate effect substantially. Thus the two alterations at positions 38 and 41 are sufficient to confer most of the bicarbonate ion effect on human beta globin. These results unequivocally show that the binding site for bicarbonate ion is located at the $\alpha_1\beta_2$ interface and the Lys-38 β and Tyr-41 β residues are important for bicarbonate ion binding.

The introduction of these two mutations into human β globin will result in a modified human haemoglobin which displays a large bicarbonate effect and will therefore be more efficient in delivering oxygen when used as an artifical blood substitute. In this way it should be possible to deliver the same amount of oxygen with a lesser dose of haemoglobin and thus reduce the effective cost and potential side effects of such an artificial oxygen carrier.

Ideally the β globin should also contain a mutation at position 108 (Asn→Lys). This is known as the Presbyterian mutation (a naturally occurring mutant form of human haemoglobin) and results in increasing the Bohr effect (the pH-dependency of haemoglobin's $O_2$ affinity). The mutant β chains are preferably co-expressed with human di-α globin dimers (as described, for example, by Looker et al., 1992 Nature 356, 258–260) to make a stable (substantially human) haemoglobin molecule with desirable properties. As the molecule would contain only 2 β globin residues from a non-human haemoglobin it would be predicted to have virtually no immunogenic capacity.

Having demonstrated the potential to modify human β globin in this way using crocodile haemoglohin it should be possible to use residues in the region β globin 29–41 from other species' haemoglohin to introduce the $CO_2$ effect from other animals into human β globin.

EXAMPLE 2

The results presented in Example 1 showed that it was possible to introduce a substantial (but not a full) bicarbonate effect into human haemoglobin by making alterations at certain residues in the β globin chain, indicating that additional changes in the α globin subunit may also be desirable.

In order to find the minimal number of crocodile residues required to create the bicarbonate effect in human haemoglobin, the present inventors humanized the α globin sequence in chimeric haemoglobin, (α(crocodile)$_2$α(SC4)$_2$) stepwise. The number of crocodile residues remaining in the α subunit could be reduced to just 7 without losing the full bicarbonate effect. This new engineered haemoglobin, named haemoglobin Scuba, consists of human α subunits with the substitutions Leu-34α→Cys, Ser-35α→Ala, Phe-36α→Tyr, Thr-37α→Gln, Thr-41α→Ile, Leu-100α→Phe, His-103α→Gln mutations and the β(SC4) subunits. Without the Leu-100α→Phe and His 103α→Gln mutations this engineered haemoglobin loses not only some of the bicarbonate effect, but also some of the cooperative oxygen binding effect.

Figure 3B:
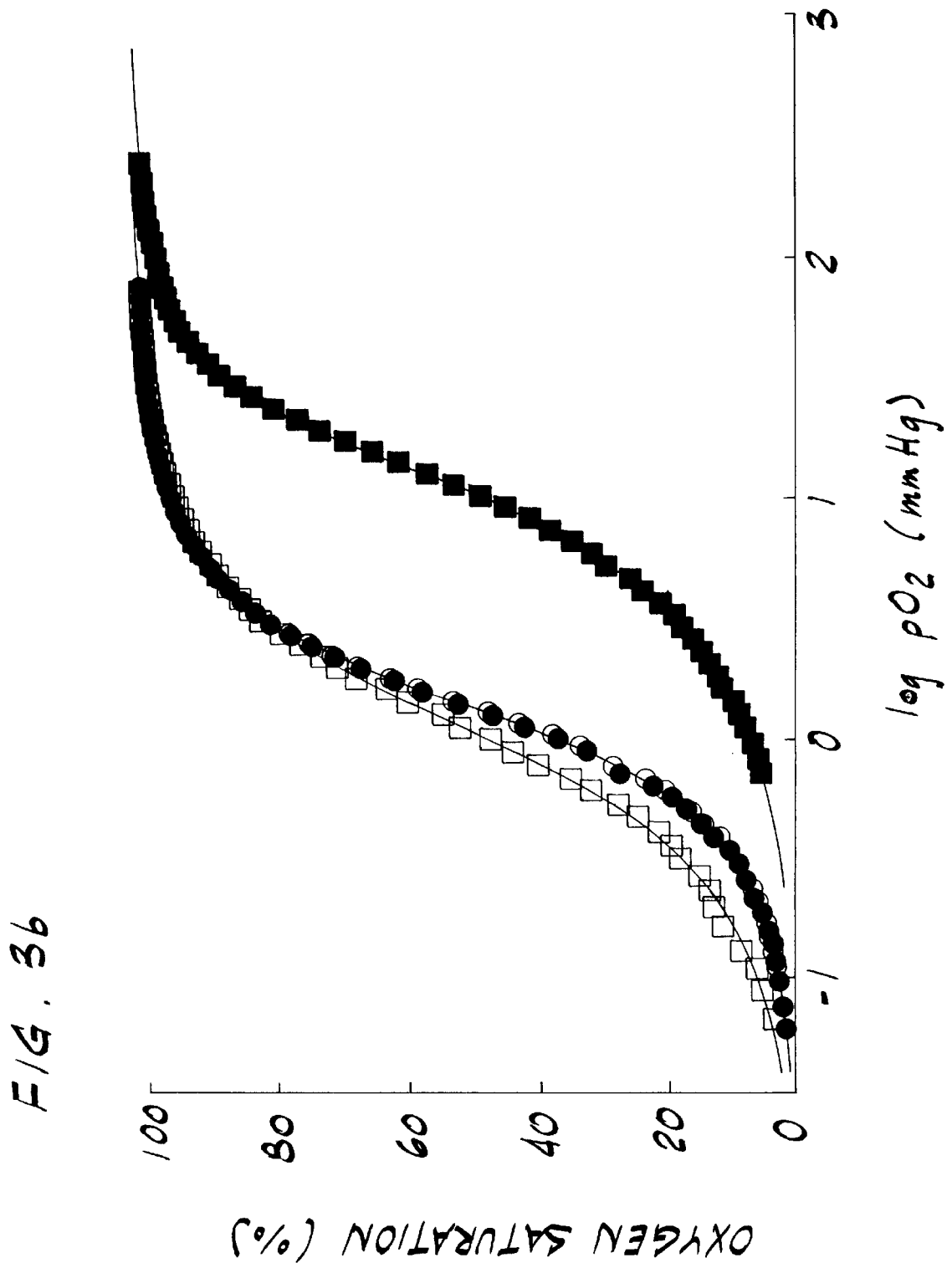
FIG. 3b is a similar graph comparing the oxygen binding curves of hybrid α(crocodile)$_2$/β(human)$_2$ (circles) and α(crocodile)$_2$/β(SC4)$_2$ (squares) haemoglobins.
Figure 3C:
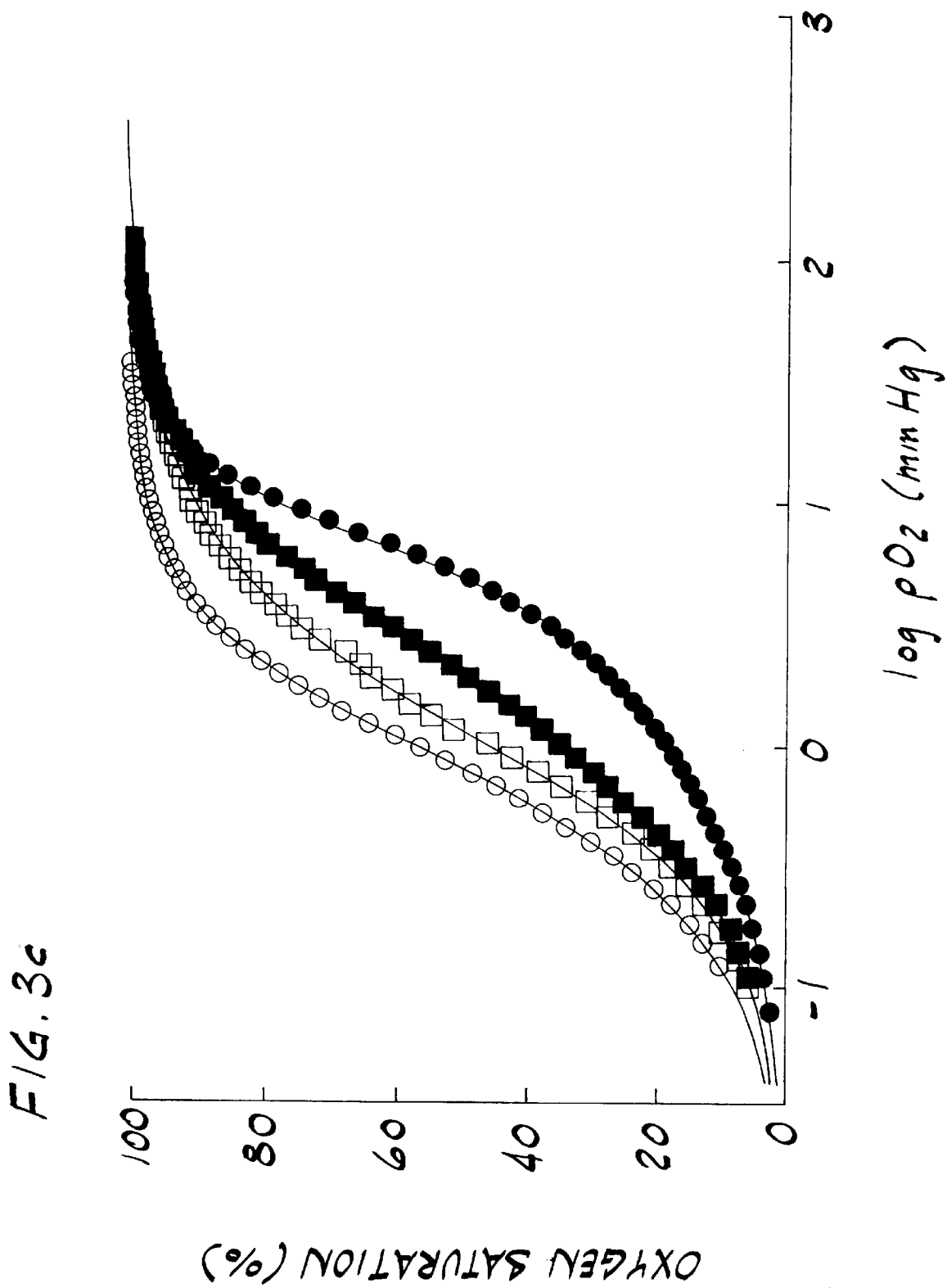
FIG. 3c is a similar graph comparing the oxygen binding curve of recombinant "Scuba" haemoglobin with (circles) or without (squares) alterations at residues 100α and 103α.

Typical results are shown in FIGS. 3a–3c.

FIG. 3a compares the oxygen binding curve for recombinant crocodile haemoglobin (circles) with that for human haemoglobin (squares), in the presence (filled symbols) or absence (open symbols) of 5% $CO_2$. The crocodile haemoglobin exhibits a large bicarbonate effect with a considerable "shift" of the curve to the left in the presence of 5% $CO_2$, indicating a greatly reduced oxygen affinity, whilst the shift for the human haemoglobin plot is very much smaller.

FIG. 3b compares the curves for the hybrid haemoglobins: α(crocodile)$_2$/β(human)$_2$ (circles) and β(crocodile)$_2$/β (SC4)$_2$. The former shows no bicarbonate effect, whilst the bicarbonate effect of the latter hybrid is almost as great as that exhibited by recombinant crocodile haemoglobin.

Figure 4:
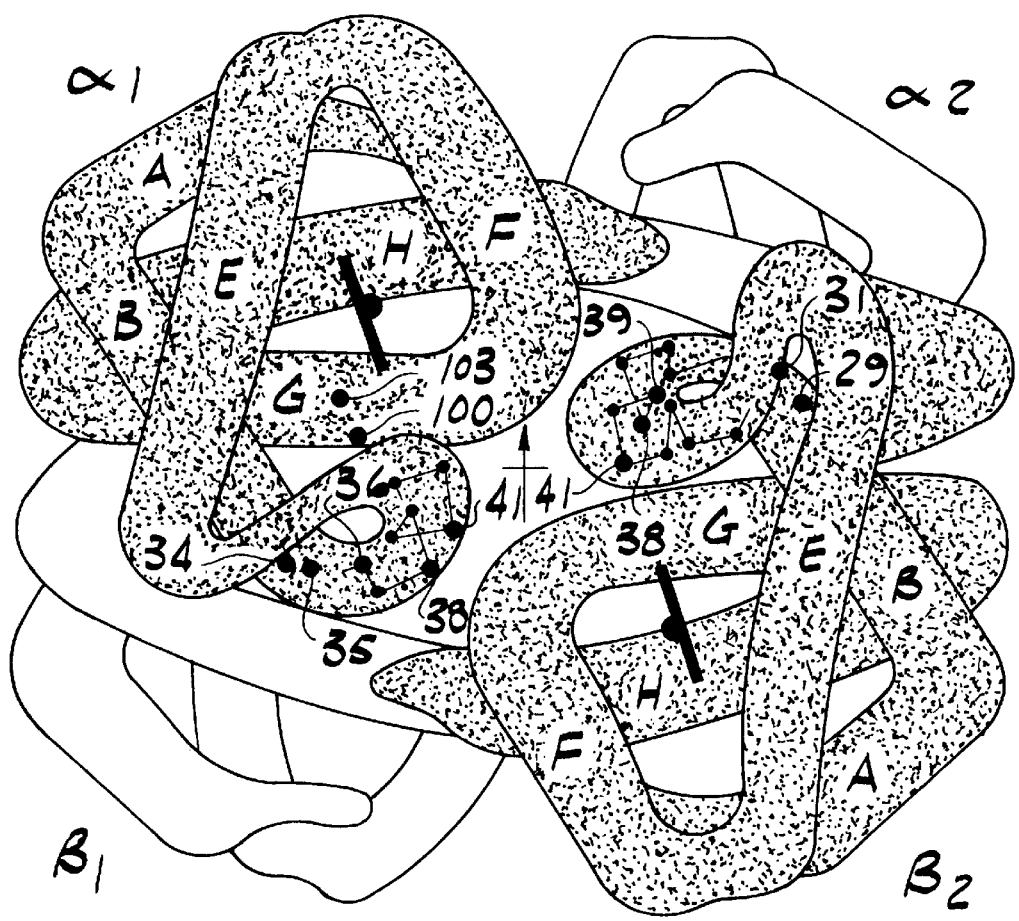
FIG. 4 is a schematic representation of human deoxyhaemoglobin.

FIG. 3c shows the oxygen binding curves for haemoglobin scuba with (circles) or without (squares) the Leu 100α→Phe and His 103α→Gln substitutions, in the absence (open symbols) or presence (filled symbols) of 5% $CO_2$ Although haemoglobin Scuba retains the full bicarbonate effect its oxygen affinity is one order of magnitude higher than that of Nile crocodile haemoglobin, both in the presence and absence of $CO_2$ (FIG. 3c). Additional mutations are therefore desirable to lower the oxygen affinity. FIG. 4 shows a schematic drawing of human deoxyhaemoglobin in which the position of the 12 mutations in haemoglobin scuba are shown. Most of these residues are clustered at the $α_2β_2$ subunit interface where the two subunits slide with respect to each other upon oxygen binding. Perutz and Fermi (Personal communication) have modelled a stereochemically plausible binding site consisting of the two mutant residues Lys-38 and Tyr-41 β, together with the conserved Tyr-42 α, but crystallographic analysis of Hb Scuba in the presence of bicarbonate ions is necessary to determine the precise binding site.

---

We claim:

1. A mutant human β globin modified to contain, at positions 29–41, at least two non-wild type amino acid residues selected from the group consisting of amino acid residues 29–41 of crocidile β globin SEQ.ID.NO: 2 to produce an enhanced bicarbonate effect.

2. The mutant β globin of claim 1, wherein said mutant β globin is having at least two amino acid substitutions selected from the group consisting of Val 33→Ile, Thr 38→Lys, Gln 39→Arg and Phe 41→Tyr.

3. The mutant β globin according to claim 2, comprising substitutions at residues 38 and 41.

4. A haemoglobin molecule, comprising the β globin of claim 1.

5. A pharmaceutical composition comprising the haemoglobin molecule of claim 4.

6. The pharmaceutical composition of claim 5, wherein said haemolgobin molecule comprises a mutant human β globin having at least two amino acid substitutions selected from the group consisting of Val 33→Ile, Thr 38→Lys, Gln 39→Arg and Phe 41→Tyr.

* * * * *

UNITED STATES PATENT AND TRADEMARK OFFICE
CERTIFICATE OF CORRECTION

PATENT NO : 5,942,488
DATED : August 24, 1999
INVENTOR(S): Noboru Komiyama et al.

It is certified that error appears in the above-identified patent and that said Letters Patent is hereby corrected as shown below:

Column 15, claim 1, line 18, "crocidile" should read ---crocodile---.

Column 15, claim 2, line 21, "globin is having at" should read ---globin has at---.

Column 16, claim 6, line 19, "haemolgobin" should read ---haemoglobin---.

Signed and Sealed this

First Day of August, 2000

Q. TODD DICKINSON

*Attest:*

*Attesting Officer*

*Director of Patents and Trademarks*